US011129643B2

(12) United States Patent
Gill et al.

(10) Patent No.: US 11,129,643 B2
(45) Date of Patent: Sep. 28, 2021

(54) NEUROSURGICAL APPARATUS

(71) Applicant: RENISHAW PLC, Wotton-under-Edge (GB)

(72) Inventors: Steven S Gill, Bristol (GB); Attila Antalfy, Ely (GB)

(73) Assignee: RENISHAW PLC, Wotton-under-Edge (GB)

( * ) Notice: Subject to any disclaimer, the term of this patent is extended or adjusted under 35 U.S.C. 154(b) by 388 days.

(21) Appl. No.: 14/379,064

(22) PCT Filed: Feb. 27, 2013

(86) PCT No.: PCT/EP2013/053972
§ 371 (c)(1),
(2) Date: Aug. 15, 2014

(87) PCT Pub. No.: WO2013/127884
PCT Pub. Date: Sep. 6, 2013

(65) Prior Publication Data
US 2015/0011938 A1    Jan. 8, 2015

(30) Foreign Application Priority Data
Feb. 28, 2012 (GB) ................................ 1203426

(51) Int. Cl.
*A61M 39/02*   (2006.01)
*A61B 17/34*   (2006.01)
(Continued)

(52) U.S. Cl.
CPC ...... *A61B 17/3415* (2013.01); *A61B 17/3423* (2013.01); *A61B 90/11* (2016.02);
(Continued)

(58) Field of Classification Search
CPC .. A61M 2210/0693; A61M 2005/1406; A61M 2039/025; A61M 2210/0687;
(Continued)

(56) References Cited

U.S. PATENT DOCUMENTS 4,798,586 A * 1/1989 Stevens .......... A61B 17/320758
604/103.1
4,944,729 A   7/1990 Buckberg et al.
(Continued)

FOREIGN PATENT DOCUMENTS

JP   2010-531693 A   9/2010
WO   WO 01/78814 A1   10/2001
(Continued)

OTHER PUBLICATIONS

Oct. 8, 2015 Chinese Office Action issued in Chinese Patent Appliction No. 201380011450.4.
(Continued)

*Primary Examiner* — Nathan R Price
*Assistant Examiner* — Courtney B Fredrickson
(74) *Attorney, Agent, or Firm* — Oliff PLC

(57) ABSTRACT

A neurosurgical apparatus includes a guide device and a neurosurgical instrument is disclosed. The guide device includes a tube for insertion into the brain and a head attached to the proximal end of the tube for affixing the guide device to a hole formed in the skull. The head has a passageway therethrough in communication with the bore of the tube such that the bore of the tube and the passageway through the head define an internal channel through which a neurosurgical instrument can be passed into the brain of the subject. The neurosurgical instrument is for insertion to a desired brain target through the internal channel of the guide device. The apparatus includes one or more sealing elements for providing a fluid tight seal between the internal channel (Continued)

Figure 1:
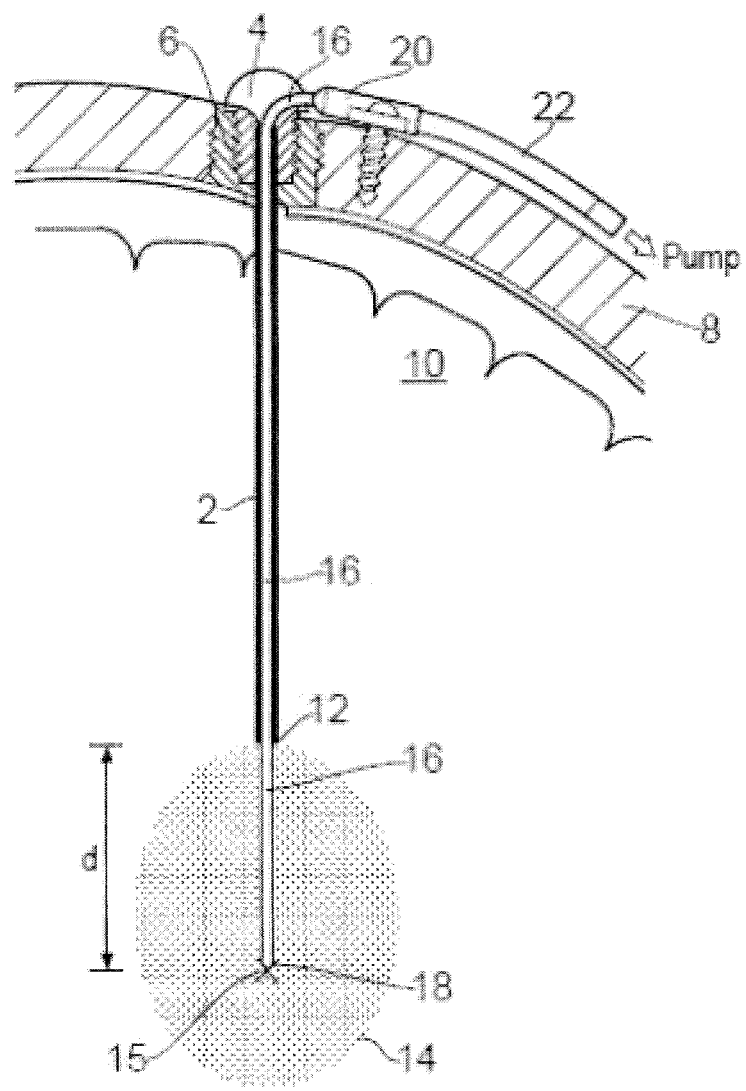

of the guide device and the exterior of the neurosurgical instrument to prevent fluid leakage from guide tube.

17 Claims, 6 Drawing Sheets

(51) Int. Cl.
*A61M 25/02* (2006.01)
*A61B 90/11* (2016.01)
*A61M 39/00* (2006.01)
*A61M 5/14* (2006.01)
*A61B 90/00* (2016.01)

(52) U.S. Cl.
CPC ............ *A61M 25/02* (2013.01); *A61M 39/02* (2013.01); *A61M 39/0247* (2013.01); *A61B 2090/034* (2016.02); *A61M 2005/1406* (2013.01); *A61M 2025/0286* (2013.01); *A61M 2039/0072* (2013.01); *A61M 2039/0205* (2013.01); *A61M 2039/025* (2013.01); *A61M 2039/027* (2013.01); *A61M 2039/0261* (2013.01); *A61M 2039/0273* (2013.01); *A61M 2039/0276* (2013.01); *A61M 2039/0279* (2013.01); *A61M 2210/0687* (2013.01); *A61M 2210/0693* (2013.01)

(58) Field of Classification Search
CPC .. A61M 2039/0273; A61M 2039/0261; A61M 2025/0293; A61B 2090/103; A61B 17/3415
See application file for complete search history.

(56) References Cited

U.S. PATENT DOCUMENTS

| | | | |
|---|---|---|---|
| 5,250,034 A | | 10/1993 | Appling et al. |
| 5,800,390 A | * | 9/1998 | Hayakawa ............ A61M 37/00 424/423 |
| 6,609,020 B2 | | 8/2003 | Gill |
| 8,251,923 B2 | | 8/2012 | Carrez et al. |
| 2001/0014787 A1 | * | 8/2001 | Toyokawa ........ A61M 25/0637 604/167.01 |
| 2004/0158136 A1 | | 8/2004 | Gough et al. |
| 2005/0154297 A1 | * | 7/2005 | Gill ........................ A61M 25/00 600/431 |
| 2006/0173440 A1 | * | 8/2006 | Lamson ............... A61M 5/3291 604/506 |
| 2009/0143764 A1 | | 6/2009 | Nelson |
| 2009/0198218 A1 | * | 8/2009 | Gill ........................ A61L 31/028 604/524 |
| 2010/0312193 A1 | | 12/2010 | Stratton et al. |
| 2012/0041392 A1 | * | 2/2012 | Donawick ......... A61M 25/0612 604/267 |
| 2012/0227746 A1 | * | 9/2012 | Harrington ........... A61M 16/04 128/207.14 |
| 2012/0316500 A1 | * | 12/2012 | Bierman ........... A61M 25/0662 604/164.1 |

FOREIGN PATENT DOCUMENTS

| | | |
|---|---|---|
| WO | WO 03/077784 A1 | 9/2003 |
| WO | WO 03/077785 A1 | 9/2003 |
| WO | WO 2008/020241 A2 | 2/2008 |
| WO | WO 2009/047491 A1 | 4/2009 |
| WO | WO 2009/047494 A1 | 4/2009 |
| WO | WO 2009/101397 A1 | 8/2009 |
| WO | WO 2013/050148 A1 | 4/2013 |

OTHER PUBLICATIONS

Apr. 26, 2016 Second Office Action issued in Chinese Patent Application No. 201380011450.4.
Search Report issued in British Patent Application No. GB1203426.0 dated May 30, 2012.
International Search Report issued in International Patent Application No. PCT/EP2013/053972 dated May 27, 2013.
Written Opinion of the International Searching Authority issued in International Patent Application No. PCT/EP2013/053972 dated May 27, 2013.
Oct. 25, 2016 Office Action issued in Chinese Patent Application No. 201380011450.4.
Apr. 13, 2017 Office Action issued in Chinese Patent Application No. 201380011450.4.
Apr. 3, 2017 Office Action issued in Japanese Patent Application No. 2014-558157.
Oct. 26, 2018 Office Action issued in Canadian Patent Application No. 2,864,624.

* cited by examiner

NEUROSURGICAL APPARATUS

The present invention relates to apparatus for neurosurgery and in particular to improved guide tube and catheter apparatus in which reflux effects are reduced.

U.S. Pat. No. 6,609,020 describes a guide device comprising a head that can be affixed to a burr hole formed in the skull and an elongate tube attached to the head. In use, the guide device is inserted into the brain towards a desired target and the head is affixed to the burr hole formed in the skull. Neurosurgical instruments (e.g. catheters, electrodes etc) may then be inserted through the guide device to a desired target. A fine catheter for use with such a guide device is also described in WO2003/077785.

The present inventors have found that a problem can arise when using a guide device system as described above, especially when dispensing fluid through a catheter. Fluid has been found to reflux along the internal lumen of the guide tube, (between the internal wall of the guide tube and the inserted catheter) and exit the head of the guide tube outside of the cranial cavity. This can reduce the amount of fluid delivered to the desired target and can also alter the extent or shape of fluid delivery to the brain.

According to a first aspect of the invention, there is provided neurosurgical apparatus comprising; a guide device comprising a tube for insertion into the brain of a subject and a head attached to the proximal end of the tube for affixing the guide device to a hole formed in the skull, the head having a passageway therethrough in communication with the bore of the tube, wherein the bore of the tube and the passageway through the head define an internal channel through which a neurosurgical instrument can be passed into the brain of the subject, and a neurosurgical instrument for insertion to a desired brain target through the internal channel of the guide device, characterised in that the apparatus comprises one or more sealing elements for providing a substantially fluid tight seal between the internal channel of the guide device and the exterior of the neurosurgical instrument when inserted therein.

The present invention thus relates to neurosurgical apparatus comprising a guide device and a neurosurgical instrument, such as a catheter. The guide device comprises an elongate tube having a head at its proximal end. In use, the elongate tube is inserted into the brain towards a target via a hole formed in the skull and the head is used to securely attach the guide device to the skull. This insertion may be performed using a stereoguide or surgical robot based technique. An internal channel is provided through the head and bore of the tube. The neurosurgical instrument (e.g. a catheter) can then be passed down this channel and into the brain in the vicinity of the selected target.

The apparatus of the present invention also comprises one or more sealing elements. The sealing elements allow, when the neurosurgical instrument is inserted into the guide device, a substantially fluid tight seal to be established between the internal channel of the guide device and the exterior of the inserted neurosurgical instrument. The sealing elements may be provided as appropriately shaped portions or regions of the guide device and/or the neurosurgical instrument. For example, the guide tube and neurosurgical instrument may be shaped, profiled or otherwise configured to fit together in a way that provides the fluid tight seal. Alternatively, one or more separate sealing elements (e.g. o-rings, washers etc) may be appropriately located between the guide device and the neurosurgical instrument.

The apparatus of the present invention thus provides a fluid tight seal between an inner surface of the internal channel of the guide device and the outer surface of the inserted neurosurgical instrument. This fluid tight seal prevents fluid flow along the inside of the guide device in the gap between the internal surface of the internal channel and the outer surface of an inserted neurosurgical instrument. For example, if the inserted neurosurgical instrument is a catheter for delivering fluid to a target site reflux back along the guide device is prevented. In particular, it prevents leakage of fluid from the intracranial cavity through the passageway of the head of the guide device.

As explained above, any suitable sealing element or elements may be used to provide the fluid tight seal. Advantageously, the one or more sealing elements comprise a tapered outer surface of the neurosurgical instrument that seals against the inner surface of the internal channel of the guide device when the neurosurgical instrument is inserted therein. The tapered outer surface of the neurosurgical instrument preferably comprises a tapered decrease in outer diameter when passing from the proximal to distal end of the instrument. Conveniently, the one or more sealing elements comprise a tapered inner surface of the internal channel of the guide device that seals against the neurosurgical instrument when the neurosurgical instrument is inserted into the guide device. The tapered innermost surface of the guide device preferably comprises a tapered decrease in internal diameter when passing from the proximal to distal end of the guide device. The neurosurgical instrument alone may comprise a tapered outer surface for engagement with a non-tapered guide device. Alternatively, the guide device alone may comprise a tapered innermost surface for engagement with a non-tapered neurosurgical instrument. In a preferred embodiment, the one or more sealing elements comprise a tapered outer surface of the neurosurgical instrument and a correspondingly tapered inner surface of the internal channel of the guide device. In other words, the neurosurgical instrument and guide device preferably include tapered surfaces that are dimensioned to engage and provide a fluid tight seal. Preferably, the taper comprises a smooth (e.g. non-stepped) change in diameter.

The neurosurgical instrument may, for example, comprise an electrode, needle, rod or any other suitable neurosurgical device. Advantageously, the neurosurgical instrument comprises a catheter. The neurosurgical instrument may be formed as a single component or may comprise a plurality of parts. For example, the neurosurgical instrument may comprise a plurality of concentric components (e.g. an inner tube and one or more outer tubes) that when assembled provide a catheter device.

As mentioned above, the neurosurgical instrument may comprise a catheter. The catheter conveniently comprises a hub. The hub may be connected to a length of fine tubing for insertion into the brain. The hub may comprise a tapered outer surface that provides a sealing element. The sealing element of the catheter may be configured for engagement with a corresponding taper provided in the passageway of the head of the guide device. Advantageously, the tapered outer surface of the hub and the corresponding taper of the passageway act as a depth stop. The depth stop may control the depth of insertion of the fine tubing into the brain. In other words, the corresponding tapers may engage and prevent further insertion of the catheter into the guide device. The length of fine tubing may thus be cut to a length that ensures the distal end (tip) of the catheter reaches a desired target site within the brain.

The hub conveniently comprises a body portion. The tapered outer surface of the hub may be located between the fine tubing and the body portion. The hub may also comprise at least one protruding wing. Conveniently, a pair of protruding wings may be provided. The at least one protruding wing is preferably configured (e.g. shaped and positioned) to engage the head of the guide device on over-insertion of the catheter into the guide device, thereby acting as a safety stop. In particular, the at least one protruding wing prevents the portion of the catheter between the tapered outer surface and the at least one protruding wing from buckling, deforming or splitting if further force is applied after the tapered outer surface of the hub has engaged the corresponding taper of the passageway. The at least one protruding wing preferably also provides a visual indication that the desired depth of catheter insertion into the guide device has been achieved. For example, the at least one protruding wing may be spaced apart from the head by a small preset distance (e.g. 0.5 mm) when the tapered outer surface of the hub and the corresponding taper of the passageway have engaged to stop further catheter insertion. The at least one protruding wing ensures that the maximum over-insertion equals the preset distance (e.g. 0.5 mm); i.e. the at least one protruding wing engages the head if over-insertion of more than the preset distance is attempted. In this manner, the apparatus is much less likely to be incorrectly implanted or damaged during implantation.

The hub of the catheter preferably comprises a fluid passageway in communication with the lumen or bore of the fine tubing. Advantageously, the fluid passageway of the hub links the fine tubing to the distal end of a connector tube. The proximal end of such a connector tube may be connected to the outlet of a fluid pump. The connector tube may be directly connected to the outlet of the fluid pump. The connector tube may be indirectly connected to the outlet of the fluid pump, via further tubing, ports, connectors etc.

The catheter advantageously comprises fine tubing for insertion into the brain that has an outer diameter of less than 1 mm. Preferably, the outer diameter is less than 0.7 mm. Preferably, the internal diameter of the fine tubing is greater than 0.2 mm or more preferably greater than 0.3 mm. An internal diameter of between 0.3 mm and 0.5 mm is preferred. The internal diameter of the fine tubing is preferably invariant through any externally tapered part of the hub.

Although a catheter arrangement is described in detail herein, it should be remembered the invention can be used for any neurosurgical instrument. The neurosurgical instrument may advantageously comprise at least one protruding wing for securing the neurosurgical instrument to the skull after insertion. The wing(s) may comprise one or more holes that allow attachment to the skull using bone screws. As mentioned above, such a wing or wings may also or alternatively be used as an over-insertion or safety stop and/or to provide a visual indication of depth of neurosurgical insertion into the guide device.

The apparatus may be formed from any suitable material. Advantageously, the apparatus is suitable for long term implantation in a subject. Preferably, at least one of the guide device and neurosurgical instrument comprises a polyurethane plastic, such as Carbothane. Carbothane has been found to be particularly resistant to blockage during long term implantation.

The one or more sealing elements may be placed at any suitable location along the length of the apparatus. Sealing elements may be placed at a plurality of locations along the length of the apparatus. For example, sealing elements may be spaced apart along the guide device. Advantageously, the one or more sealing elements are provided in the vicinity of the head of the guide device. This is preferred because the larger size of the head (compared to the tube) permits a more robust seal to be provided. In particular, a tapered section in the vicinity of the head can be made to be less deformable than a taper formed further along the tube.

Conveniently, one or more features are provided on the external surface of the head of the guide device for securing the guide device to a hole formed in the skull. The features may comprise ribs. The features may comprise a screw thread. The features may enable the head to be press fitted into a hole formed in the skull. The head of the guide device may comprise a slot. The slot allows an inserted instrument to be bent so that it exits from the head in a direction orthogonal to the longitudinal axis of the tube of the guide device (i.e. it allows an inserted device to be bent so as to lie parallel to bone). The provision of a slot with screw thread formations allows the guide device to be unscrewed from the skull.

The apparatus may include other components. For example, it may comprise a fluid pump (e.g. a fluid pump for convection enhanced delivery), a port (e.g. a percutaneous access port) a fluid connector and/or a filter (e.g. a bubble and/or bacterial filter).

The invention also extends to a guide device modified to provide a fluid seal with a neurosurgical instrument inserted therein. An aspect of the invention thus provides a guide device comprising; a tube for insertion into the brain of a subject and a head attached to the proximal end of the tube for affixing the guide device to a hole formed in the skull, the head having a passageway therethrough in communication with the bore of the tube, wherein the bore of the tube and the passageway through the head define an internal channel through which a neurosurgical instrument can be passed into the brain of the subject, wherein the guide device is arranged to receive an associated neurosurgical instrument for insertion to a desired brain target through the internal channel of the guide device, characterised in that the guide device comprises one or more sealing elements for providing a substantially fluid tight seal between the internal channel of the guide device and the exterior of an associated neurosurgical instrument when inserted therein. The guide device may have any of the other features described in more detail above.

The invention also extends to a neurosurgical instrument (e.g. a catheter or electrode) modified to provide a fluid seal with a guide device when it is inserted therein. An aspect of the invention thus provides a neurosurgical instrument for insertion to a desired brain target through an associated guide device that comprises a tube for insertion into the brain of a subject and a head attached to the proximal end of the tube for affixing the guide device to a hole formed in the skull, the head having a passageway therethrough in communication with the bore of the tube, wherein the bore of the tube and the passageway through the head define an internal channel through which the neurosurgical instrument can be passed into the brain of the subject, characterised in that the neurosurgical instrument comprises one or more sealing elements for providing a substantially fluid tight seal with the internal channel of the associated guide device. The neurosurgical instrument may have any of the other features described in more detail above.

The invention also extends to a method of surgically implanting apparatus as described above. The apparatus may be implanted in a human patient or in an animal. The invention thus extends to a method of inserting a neurosurgical instrument to a target in the brain of a subject using neurosurgical apparatus as described above, the method comprising the steps of; (i) forming a hole in the skull of the subject, (ii) inserting the tube of the guide device into the brain and engaging the head with the hole formed in the skull thereby securing the guide device in place, (iii) passing the neurosurgical instrument through the internal channel of the guide device until the distal end of the neurosurgical instrument is located at the desired brain target. Advantageously, suction is applied to the head of the guide device during the insertion process of step (iii) to prevent fluid (e.g. air bubbles) being driven into the brain. The fluid seal established between the neurosurgical instrument and the guide device during step (iii) preferably reduces or prevents fluid reflux back through the guide device. The method may use any suitable guidance technique for inserting the guide device and neurosurgical instrument. For example, a surgical robot or manual stereoguide may be used.

The neurosurgical instrument inserted into the guide device is preferably a catheter. The method may then comprise a step of delivering fluid to the brain through the implanted catheter. The fluid may comprise any pharmaceutical composition for treating a neurological condition or a cytotoxic agent for oncology. The method may comprise delivering a growth factor, such as GDNF, or a viral vector. Delivery of fluid may be continuous or intermittent. The apparatus may be used to treat acute or chronic conditions. The apparatus, or part thereof, may be explanted after delivery. Alternatively, the apparatus (e.g. the guide device) may be left implanted long-term (e.g. for the rest of the subject's life).

Figure 2:
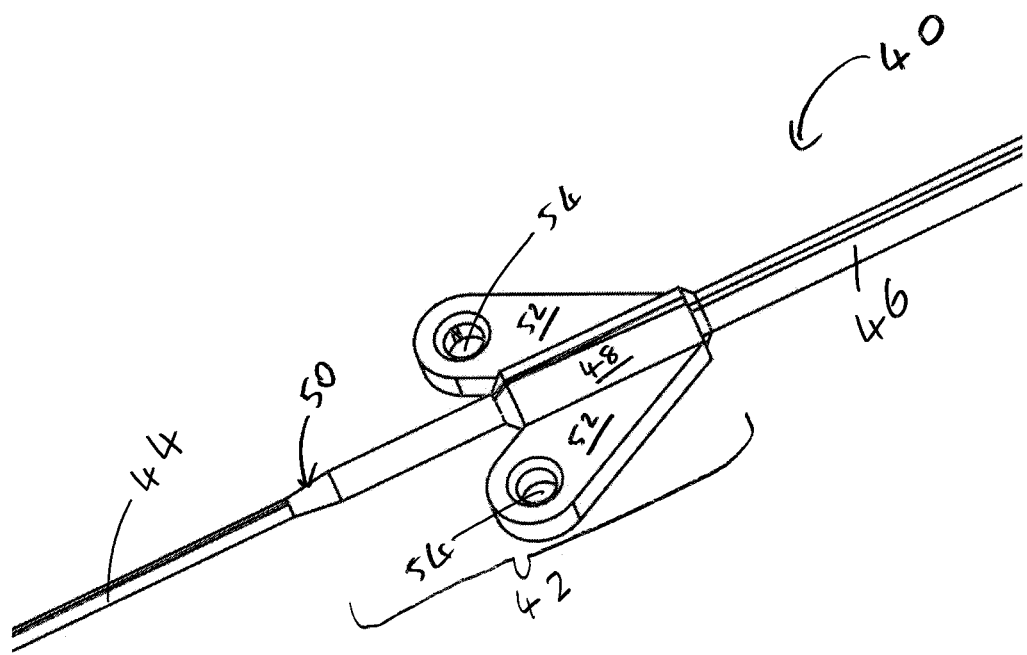
Figure 3:
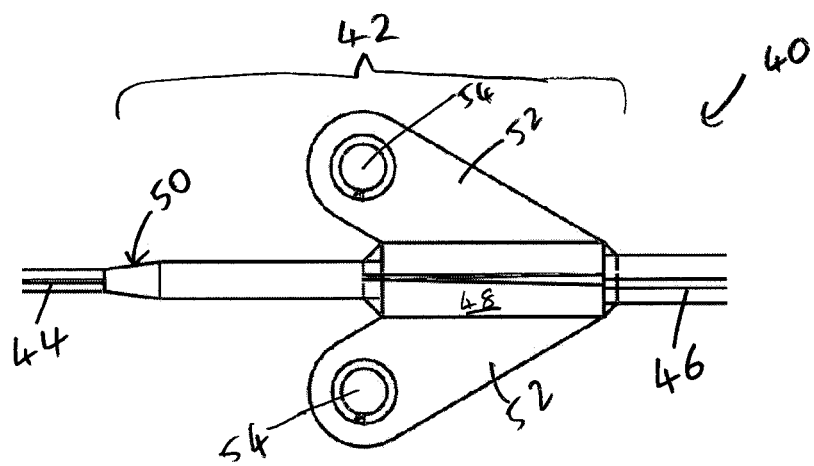
Figure 4:
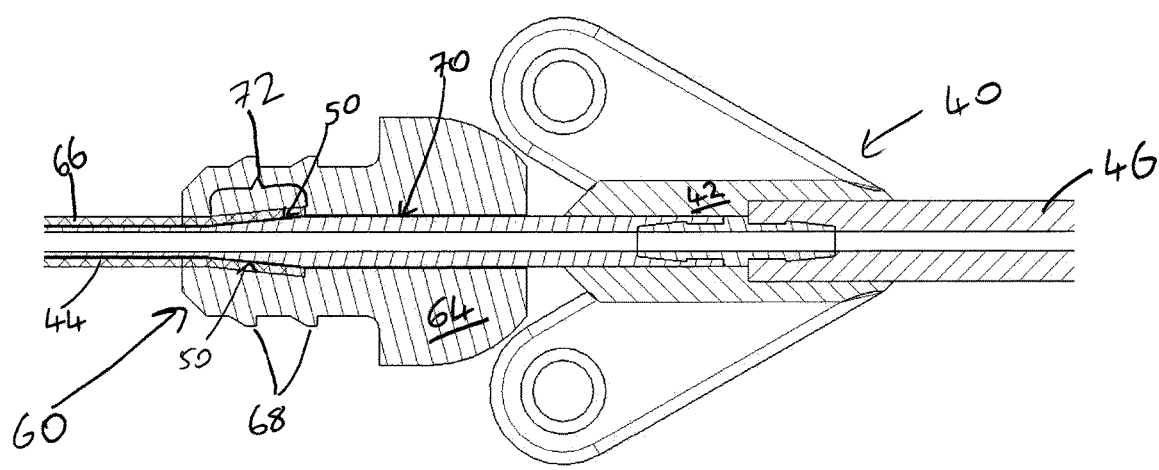
Figure 5:
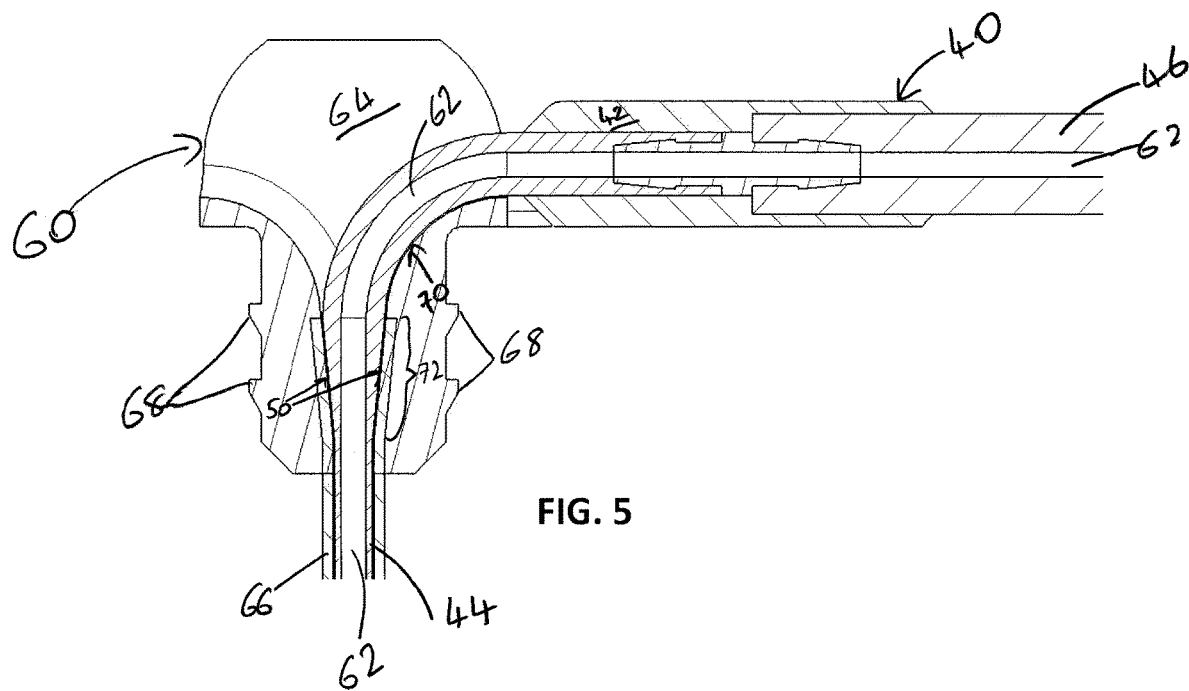
Figure 6:
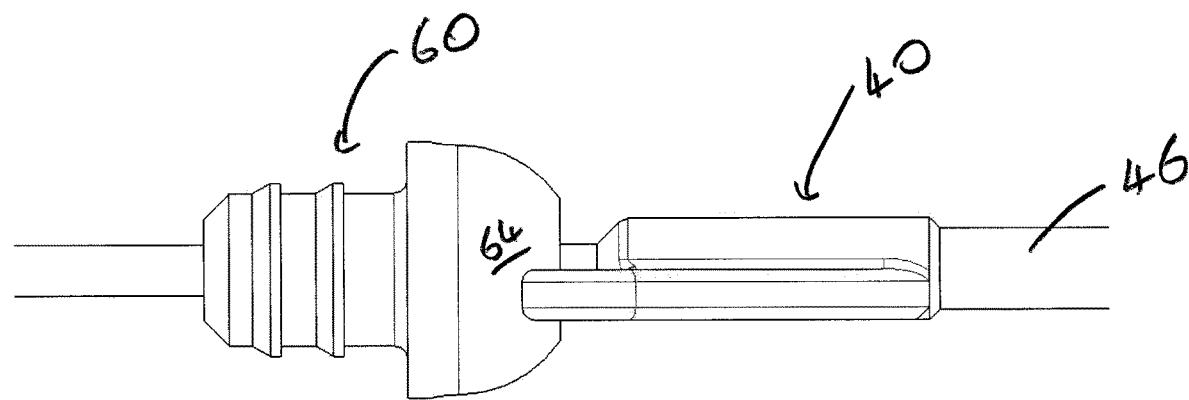
Figure 7:
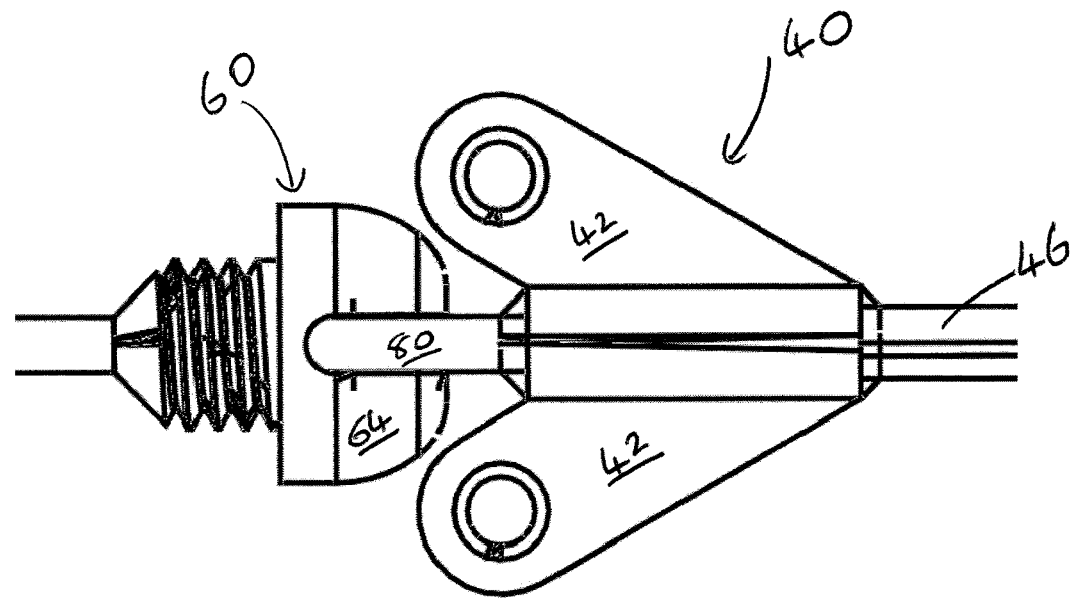
Figure 8:
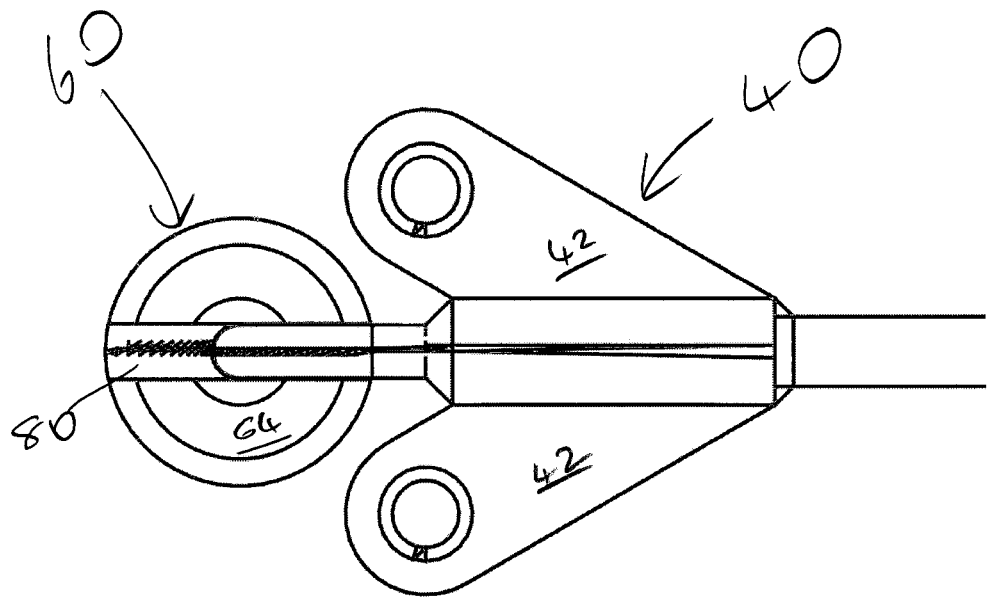
Figure 9:
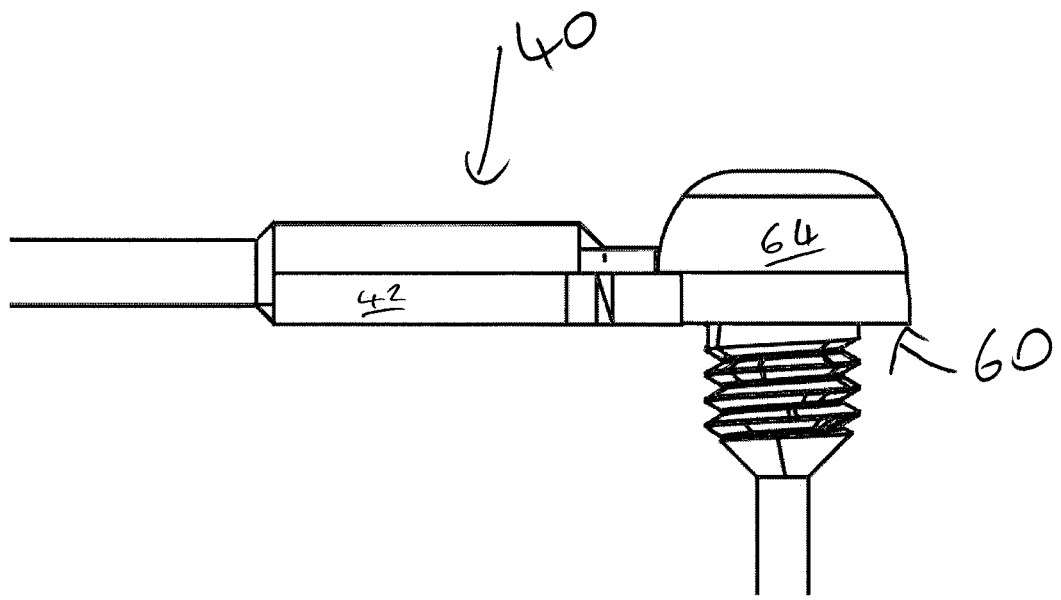
Figure 10:
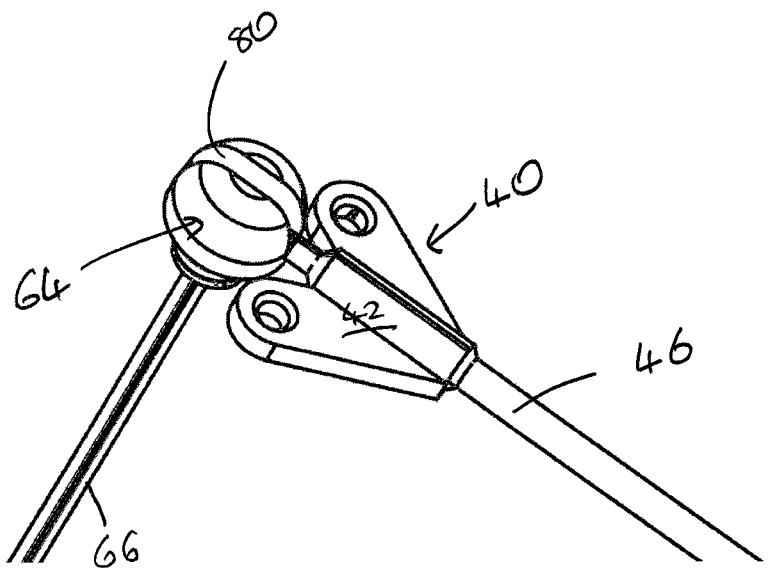
Figure 11:
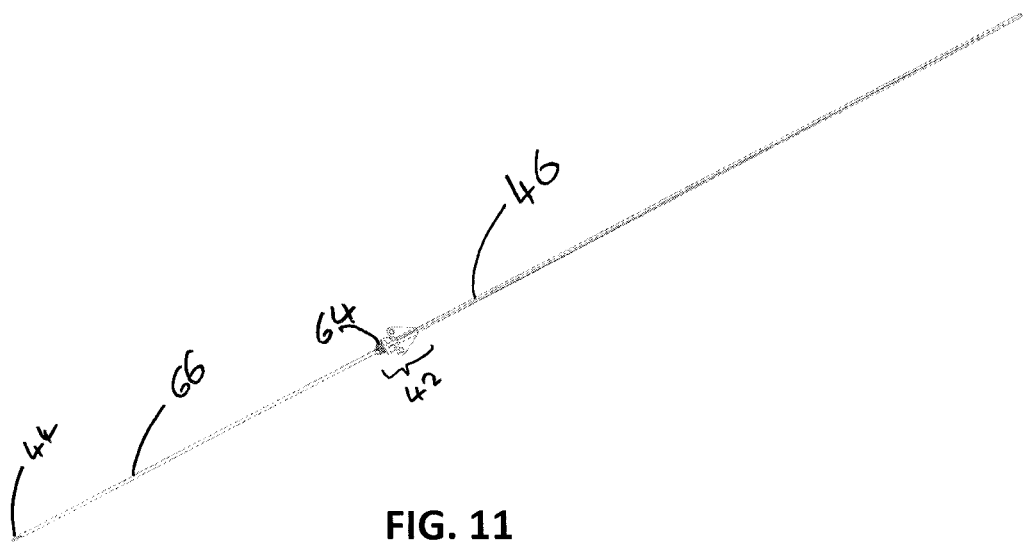

The invention will now be described, by way of example only, with reference to the accompanying drawings in which;

FIG. 1 illustrates a prior art neurosurgical catheter and guide tube arrangement, FIG. 2 shows a catheter of the present invention, FIG. 3 shows an alternative view of the catheter of FIG. 2, FIG. 4 shows a catheter of the present invention inserted into a guide tube of the present invention, FIG. 5 shows the catheter and guide tube of FIG. 4 after the catheter has been bent following implantation, FIG. 6 is an external view of the catheter and guide tube of the present invention, FIG. 7 is an alternative view of the catheter and guide tube of the present invention, FIG. 8 is a further alternative view of the catheter and guide tube of the present invention, FIG. 9 is a further alternative view of the catheter and guide tube of the present invention, FIG. 10 is a further alternative view of the catheter and guide tube of the present invention, and FIG. 11 shows the full length of the catheter and guide tube of the present invention.

Referring to FIG. 1, a prior art implanted fluid delivery system of the type described in WO2003/077785 is illustrated.

The fluid delivery system comprises a guide device comprising an elongate tube 2 having a head 4 at its proximal end. The head 4 has an external thread 6 to allow attachment to a burr hole formed in the skull bone 8 of a subject. The guide device is inserted stereotactically into the brain parenchyma 10 using a stereoguide device. In particular, the guide device can be accurately inserted in the brain along a predefined axis of insertion such that it's distal end 12 is located just short (by a distance d) of a target point 15. More details concerning accurate (e.g. stereotactic) insertion of the guide tube can be found elsewhere; for example, see WO2003/077784, WO2003/077785 and U.S. Pat. No. 6,609,020.

After the guide device has been implanted, a flexible catheter is inserted through the head 4 and into the tube 2. The flexible catheter comprises a length of fine tubing 16 having an outside diameter of 1 mm or less. During implantation, the fine tubing 16 is inserted into the guide device 2 and advanced therethrough until the distal end 18 of the fine tube 16 protrudes a distance "d" from the distal end 12 of the tube 2 and thereby reaches the target point 15. As described in WO2003/077785, the fine tube 16 is flexible and is typically reinforced by a guide wire (not shown) during implantation to prevent the catheter significantly deviating from the required axis of insertion as it is exits the distal end 12 of the elongate tube 2 and is driven towards target point 15. Once implanted, the guide wire is withdrawn from the catheter leaving the fine tube 16 in situ.

The fine tube 16 of the catheter is connected to a hub 20 that is screwed to the outside of the skull 8. A supply or connector tube 22 is in fluid communication with the fine tube 16 via a channel formed in the hub 20. The supply tube 22 may receive fluid from a remotely located drug pump, the fluid then being routed along the fine tube 16 to the target volume 14.

Although the prior art guide tube and catheter device has been found to perform well, the present inventor has identified a potential problem. In particular, it has been found that during fluid delivery via the catheter there can be reflux of fluid along the inside of the guide device in the gap between the catheter and the guide device. This can reduce the pressure that is established at the catheter tip (potentially altering the fluid delivery profile) and may cause unwanted reflux of fluid out of the intracranial cavity.

Referring to FIGS. 2 and 3, a catheter 40 of the present invention is illustrated. The catheter 40 comprises a hub 42, a fine tube 44 and a connector tube 46. The hub 42 comprises a body portion 48, a sealing element in the form of a tube having a tapered surface 50 (which is an example of a sealing element) and a pair of protruding wings 52. The wings 52 have apertures 54 formed therein for receiving bone screws.

Referring to FIGS. 4 and 5, a catheter 40 of the type described with reference to FIGS. 2 and 3 is shown when inserted into a guide device 60 of the present invention. The catheter 40 comprises a bore or lumen 62 that runs through the connector tube 46, a hub 42 and a fine tube 44. The internal diameter of the lumen 62 is substantially constant through the catheter 40, although it could be varied if required. The guide device 60 comprises a head 64 and an elongate tube 66. The head 64 comprises external ridges 68 that allow it to be attached to a hole formed in the skull by a press fit action. The guide device 60 comprises a passageway 70 through the head 64 in which the catheter 40 can be located. As should be appreciated from FIG. 5, the substantially fluid tight seal is only provided when the catheter 40 is fully inserted into the internal channel of the guide device 60 and a distal end of the catheter 40 is at a target point in the skull.

The passageway 70 of the head 64 comprises an internally tapered region 72 (which is an example of a sealing element) that forms a fluid tight seal with the tapered surface 50 of the inserted catheter. This seal prevent fluids from passing along the gap between the fine tube 44 and the elongate tube 66 into the head 64. Fluid leakage and reflux is thus inhibited. However, as shown in FIG. 5, this seal does not obstruct the lumen 62 running through the catheter 40.

FIG. 4 shows the catheter 40 after insertion in to the guide device 60, whilst FIG. 5 shows the arrangement after the catheter has been bent through ninety degrees in the slot formed in the head 64. The wings 52 of the catheter are, when the tapered region 72 of the guide device 60 engages the tapered surface 50 of the catheter 40, arranged to be located very close (e.g. within 0.5 mm) to the head 64 of the guide device 60. This provides a visual indication that the tapered surfaces have engaged to form the fluid seal. The wings 52 and head 64 will also engage if further insertion of the catheter is attempted, thereby acting as an insertion limiter or safety stop to prevent buckling or other damage to the catheter FIGS. 6 and 7 show various external views of the catheter 40 when inserted in to the guide device 60. FIGS. 8, 9 and 10 show various external views of the catheter 40 when inserted in to the guide device 60 after the catheter 40 has been bent. In particular, FIGS. 7, 8 and 10 show the slot 80 formed in the head 64 of the guide device 60.

FIG. 11 is an overview of the combined catheter and guide tube system. The length of the elongate tube 66 and fine tube 44 can cut to any desired length to reach the required targets in the brain.

The skilled person would appreciate that the above is merely one example of the present invention and that variants to the above described embodiments would be possible. In particular, the catheter could be replaced with any suitable neurosurgical instrument, such as an electrode. The devices could also be made from any suitable material, implanted using any suitable surgical technique and used to deliver a variety of therapeutic agents.

The invention claimed is:

1. A neurosurgical apparatus comprising:
a catheter for insertion to a desired brain target; and
a guide device comprising a tube for insertion into a brain of a subject and a head attached to a proximal end of the tube for affixing the guide device to a hole formed in a skull, the head having a passageway therethrough in communication with a bore of the tube, wherein the bore of the tube and the passageway through the head define an internal channel through which the catheter can be passed into the brain of the subject, wherein:
the apparatus comprises one or more sealing elements for providing a substantially fluid tight seal between the internal channel of the guide device and an exterior of the catheter,
the one or more sealing elements comprising at least one of a tapered outer surface of the catheter and a tapered inner surface of the internal channel of the guide device,
the one or more sealing elements are provided at a distal side in the head of the guide device such that the one or more sealing elements are configured to be positioned fully within an outer surface of the skull,
the one or more sealing elements being arranged to provide the fluid tight seal between the exterior of the catheter and the internal channel of the guide device only when the catheter is fully inserted into the internal channel of the guide device such that the catheter cannot be further inserted into the internal channel of the guide device,
the catheter comprises a hub connected to a length of fine tubing for insertion into the brain, the hub comprising a tapered outer surface that provides a sealing element of the one or more sealing elements for engagement with a corresponding taper provided in the passageway of the head of the guide device, wherein the tapered outer surface of the hub and the corresponding taper of the passageway act as a depth stop for controlling a depth of insertion of the fine tubing into the brain, and
the hub also comprises a body portion, the tapered outer surface being located between the fine tubing and the body portion, wherein the hub also comprises at least one protruding wing that is spaced apart from the head by a small preset distance when the tapered outer surface of the hub and the corresponding taper of the passageway have engaged thereby providing a visual indication of engagement.

2. An apparatus according to claim 1, wherein the hub comprises a fluid passageway that links the fine tubing to a distal end of a connector tube, a proximal end of the connector tube being connected to an outlet of a fluid pump.

3. An apparatus according to claim 1, wherein the catheter comprises the fine tubing for insertion into the brain that has an outer diameter of less than 0.7 mm.

4. An apparatus according to claim 1, wherein the catheter comprises the fine tubing for insertion into the brain that has an inner diameter of more than 0.3 mm.

5. An apparatus according to claim 1, wherein at least one of the guide device and the catheter comprises a polyurethane plastic.

6. An apparatus according to claim 1, wherein one or more features are provided on an external surface of the head of the guide device for securing the guide device to the hole formed in the skull.

7. An apparatus according to claim 1, further comprising a fluid pump.

8. A neurosurgical apparatus comprising:
a catheter for insertion to a desired brain target; and
a guide device comprising a tube for insertion into a brain of a subject and a head attached to a proximal end of the tube for affixing the guide device to a hole formed in a skull, the head having a passageway therethrough in communication with a bore of the tube, wherein the bore of the tube and the passageway through the head define an internal channel through which the catheter can be passed into the brain of the subject, wherein:
the apparatus comprises one or more sealing elements for providing a substantially fluid tight seal between the internal channel of the guide device and an exterior of the catheter,
the one or more sealing elements comprising at least one of a tapered outer surface of the catheter and a tapered inner surface of the internal channel of the guide device,
the one or more sealing elements are provided at a distal side in the head of the guide device such that the one or more sealing elements are configured to be positioned fully within an outer surface of the skull,
the one or more sealing elements being arranged to provide the fluid tight seal between the exterior of the catheter and the internal channel of the guide device only when the catheter is fully inserted into the internal channel of the guide device such that the catheter cannot be further inserted into the internal channel of the guide device, and
the catheter comprises at least one protruding wing for securing the catheter to the skull after insertion.

9. An apparatus according to claim 8, wherein the one or more sealing elements include the tapered outer surface of the catheter that seals against an inner surface of the internal channel of the guide device when the catheter is inserted therein.

10. An apparatus according to claim 8, wherein the one or more sealing elements include the tapered inner surface of the internal channel of the guide device that seals against the catheter when the catheter is inserted into the guide device.

11. An apparatus according to claim 8, wherein the catheter comprises a hub connected to a length of fine tubing for insertion into the brain, the hub comprising a tapered outer surface that provides a sealing element of the one or more sealing elements for engagement with a corresponding taper provided in the passageway of the head of the guide device, wherein the tapered outer surface of the hub and the corresponding taper of the passageway act as a depth stop for controlling a depth of insertion of the fine tubing into the brain.

12. An apparatus according to claim 8, wherein the catheter comprises fine tubing for insertion into the brain that has an outer diameter of less than 0.7 mm.

13. An apparatus according to claim 8, wherein the catheter comprises fine tubing for insertion into the brain that has an inner diameter of more than 0.3 mm.

14. An apparatus according to claim 8, wherein at least one of the guide device and the catheter comprises a polyurethane plastic.

15. An apparatus according to claim 8, wherein one or more features are provided on an external surface of the head of the guide device for securing the guide device to the hole formed in the skull.

16. An apparatus according to claim 8, further comprising a fluid pump.

17. A method of inserting a catheter to a target in a brain of a subject using a neurosurgical apparatus comprising:

a catheter for insertion to a desired brain target; and a guide device comprising a tube for insertion into a brain of a subject and a head attached to a proximal end of the tube for affixing the guide device to a hole formed in a skull, the head having a passageway therethrough in communication with a bore of the tube, wherein the bore of the tube and the passageway through the head define an internal channel through which the catheter can be passed into the brain of the subject, wherein:

the apparatus comprises one or more sealing elements for providing a substantially fluid tight seal between the internal channel of the guide device and an exterior of the catheter, the one or more sealing elements comprising at least one of a tapered outer surface of the catheter and a tapered inner surface of the internal channel of the guide device, the one or more sealing elements are provided at a distal side in the head of the guide device such that the one or more sealing elements are configured to be positioned fully within an outer surface of the skull, and the one or more sealing elements being arranged to provide the fluid tight seal between the exterior of the catheter and the internal channel of the guide device only when the catheter is fully inserted into the internal channel of the guide device such that the catheter cannot be further inserted into the internal channel of the guide device, the method comprising the steps of:

(i) forming the hole in the skull of the subject, (ii) inserting the tube of the guide device into the brain and engaging the head with the hole formed in the skull thereby securing the guide device in place, (iii) passing the catheter through the internal channel of the guide device until the catheter is fully inserted into the internal channel of the guide device such that the catheter cannot be further inserted into the internal channel of the guide device, and such that the substantially fluid tight seal is only provided between the internal channel of the guide device and the exterior of the catheter when the catheter is fully inserted into the internal channel of the guide device.

\* \* \* \* \*